United States Patent
Goren et al.

(10) Patent No.: US 11,337,937 B2
(45) Date of Patent: May 24, 2022

(54) TARR RECEPTOR AGONISTS FOR SEXUAL DYSFUNCTION

(71) Applicant: ReJoy, Irvine, CA (US)

(72) Inventors: Ofer A. Goren, Irvine, CA (US); John McCoy, Irvine, CA (US)

(*) Notice: Subject to any disclaimer, the term of this patent is extended or adjusted under 35 U.S.C. 154(b) by 0 days.

(21) Appl. No.: 16/552,083

(22) Filed: Aug. 27, 2019

(65) Prior Publication Data

US 2020/0060997 A1 Feb. 27, 2020

Related U.S. Application Data

(60) Provisional application No. 62/723,170, filed on Aug. 27, 2018.

(51) Int. Cl.
| | |
|---|---|
| *A61K 31/137* | (2006.01) |
| *A61K 9/00* | (2006.01) |
| *A61P 15/00* | (2006.01) |
| *A61K 45/06* | (2006.01) |

(52) U.S. Cl.
CPC .......... *A61K 31/137* (2013.01); *A61K 9/0014* (2013.01); *A61K 45/06* (2013.01); *A61P 15/00* (2018.01)

(58) Field of Classification Search
CPC .......... A61K 31/137; A61K 9/00; A61P 15/00
See application file for complete search history.

(56) References Cited

U.S. PATENT DOCUMENTS 10,064,816 B2 * 9/2018 Goren ................. A61K 9/0009

OTHER PUBLICATIONS

Brown et al. British J. Pharmacology, 1988, vol. 93, pp. 417-429.*
Herbert, A.A., et al., Dietary trace amine-dependent vasoconstriction in porcine coronary artery, British Journal of Pharmacology, 2008, pp. 525-534, Macmillan Publishers Limited.
Koh, Andy Hsien Wei, et al., Renal artery responses to trace amines: Multiple andd differential mechanisms of actions, Life Sciences, 2021, pp. 1-8, Elsevier Inc.
Fehler, M., et al., Identification of trace-amine-associated receptors (TAAR) in the rat aorta and their role in vasoconstriction by β-phenylethylamine, Naunyn-Schmied Arch Pharmacol, 2010, 385-398, Springer-Verlag.

* cited by examiner

*Primary Examiner* — Samira J Jean-Louis
(74) *Attorney, Agent, or Firm* — Buchanan Ingersoll & Rooney PC

(57) ABSTRACT

The present invention discloses compositions, methods, and systems of treating female sexual dysfunction by stimulating the contraction of the smooth muscle of the nipple. The smooth muscle in the nipple expresses trace amine associated receptors and thus can be contracted through a class of trace amine associated receptor agonists such as octopamine or tyramine, but any agent that promotes contraction of smooth muscle can be considered for the methods and compositions described herein. The contraction of the smooth muscle erects the nipple and increases female sexual arousal. The smooth muscle stimulatory compound can be formulated in a solution, foam, ointment, gel, spray, lotion, powder, topical cream, emulsion, slow release capsule or any similar method, compound, or delivery vehicle including a pre-wetted gauze or cotton pad. Additionally, the disclosed composition can be used to improve the quality of a sexual experience, e.g., it can increase orgasm intensity or a subject's interest in sex, of females that do not suffer from sexual dysfunction.

6 Claims, No Drawings

TARR RECEPTOR AGONISTS FOR SEXUAL DYSFUNCTION

CROSS-REFERENCE TO RELATED APPLICATIONS

This application is related to and claims the benefit of U.S. Provisional Application 62/723,170 filed on Aug. 27, 2018, the entire contents of which are incorporated herein by reference.

TECHNICAL FIELD

The present invention is directed to compositions, systems and methods for increasing the quality of the female sexual experience and can be used in some cases for treating female sexual dysfunction including, but not limited to, female sexual arousal disorder (FSAD) and female hypoactive sexual desire disorder (FHSDD).

BACKGROUND

The following description includes information that may be useful in understanding the present invention. It is not an admission that any of the information provided herein is prior art or relevant to the presently claimed invention, or that any publication specifically or implicitly referenced is prior art.

Female sexual dysfunction (FSD) is an increasingly common diagnosis. FSD can be classified under many subtypes. For example, female sexual arousal disorder (FSAD) is a disorder characterized by a persistent inability to attain sexual arousal or to maintain arousal until the completion of a sexual activity. Hypoactive sexual desire disorder (HSDD) is a general loss of interest in sexual activity. Other subtypes exist, for example, anorgasmia, a difficulty achieving orgasm. Currently, there are no FDA approved treatments for FSD, however, off-label use of testosterone has been prescribed.

Additionally, improving the quality of the female sexual experience, i.e., not a treatment for a diagnosed medical condition, can be classified under many subtypes. For example, reducing the time to achieve orgasm (orgasmic latency), increasing the intensity of orgasm, and increasing the frequency of orgasm may be desired by a female who does not suffer from FSD. Other cosmetic claim examples include, erogenous zone stimulation, increase in vaginal lubrication, increasing desire, increasing sexual satisfaction, or increased arousal.

Trace amine-associated receptors (TAARs), sometimes referred to as trace amine receptors (TAs or TARs), are a class of G protein-coupled receptors found in mammals. TAARs bind trace amines found naturally in mammals, e.g., phenylethylamine, tyramine, and tryptamine; metabolic derivatives of the amino acids phenylalanine, tyrosine and tryptophan, respectively. TAARs also bind many synthetic compounds, e.g., ephedrine, amphetamine, methamphetamine, methylenedioxymethamphetamine (MDMA, ecstasy). Additionally, it has been shown that mammalian TAAR1 is also a receptor for thyronamines, decarboxylated and deiodinated relatives of thyroid hormones. TAAR2-TAAR9 have been shown to function as olfactory receptors for volatile amine odorants in vertebrates.

SUMMARY

The present invention discloses compositions, systems, and methods of treating FSD or generally improving the quality of the female sexual experience by stimulating the female nipple through the use of compounds or agents that induce contraction of the smooth muscle under control of the autonomic nervous system. During sexual arousal the female physiological response is marked by the erection of the nipples and the release of oxytocin. As oxytocin and nipple erection are intimately linked it is also found that stimulation of the nipple increases sexual arousal, orgasmic intensity and overall sexual satisfaction. Increasing any one or combination of these can lead to an improvement of the quality of an orgasm and/or an enhancement of the quality of sex or the sexual experience. Levin et al. (Levin R., Meston C., Nipple/Breast Stimulation and Sexual Arousal In Young Men and Women. J Sex Med 2006; 3: 450-454) teaches that 82% of women reported that stimulation of their nipples enhanced sexual arousal. Additionally, stimulation of the nipple enhanced sexual arousal for 40% on men. As such, compounds or agents that stimulate erection of the nipple on increase sensitivity of the nipple can increase sexual arousal and be used to treat FSD or improve the quality of the sexual experience.

Trace amines are biologically active amines occurring in the body in trace amounts. Some examples of trace amines include tyramine, beta phenylethylamine, tryptamine and octopamine. They are structurally and functionally related to the catecholamines and there are a large number of synthetic analogues, such as, amphetamines. Endogenous trace amines are synthesized in the body by the decarboxylation of their respective precursor amino acids. Oral administration of trace amines in humans cause increase in blood pressure and trace amines supplied to isolated blood vessels cause vasoconstriction. Trace amines ability to contract the smooth muscle of the nipple areola complex (NAC) are previously unreported.

While the disclosure most often specifically refers to TAAR agonists as agents useful for treating FSD or improving the quality of the female sexual experience, it should be understood that any agent that stimulates contraction of smooth muscle, and particularly the AP muscle, can be useful in the compositions and methods described herein. That is, unless specifically indicated otherwise, disclosure relating to uses or formulations of TAAR agonists should be considered to refer as well to other agents that stimulate AP muscle contraction.

In one aspect, the methods and compositions described herein take advantage of the believed expression of trace amine associated receptors (TAARs) by smooth muscle in the nipple. In this aspect, trace amine associated receptor agonists (TAARA) can be administered to the nipple to promote contraction of smooth muscle in the NAC and thereby produce an erection. The TAARA can be formulated in a foam, solution, ointment, gel, lotion, spray, powder, emulsion, slow release capsule, or any similar compound or delivery vehicle or methodology. While the disclosure most often specifically refers to trace amine associated receptor agonists as agents useful for stimulating NAC smooth muscle contraction, it should be understood that any agent that stimulates contraction of the NAC smooth muscle, and particularly causes nipple erection and/or increased nipple sensitivity, can be useful in the compositions and methods described herein. That is, unless specifically indicated otherwise, disclosure relating to uses or formulations of TAARAs should be considered to refer as well to other agents that stimulate smooth muscle contraction of the NAC.

TAARs are located in vascular smooth muscle and can be stimulated to cause smooth muscle tone changes independent of the sympathetic mechanism, e.g., alpha and beta adrenergic receptors. This new mechanism provides new avenues for methods to simulate smooth muscle modulation to augment existing sympathomimetic signaling molecules. For example, TAARs may be used as vasopressors to modulate blood flow. This may be advantageous because many of the traditionally applied alpha and beta adrenergic receptor agonists exhibit well documented "rebound" effects; TAARs have not been shown to have this limitation. Additionally, TAARs may be used to stimulate the arrector pili muscle, which is also a smooth muscle in the skin. Topical Formulations of TAAR receptors would be advantageous for application to the skin. Like topical formulations of alpha and beta adrenergic receptor effector molecules they can be utilized to modulate smooth muscle in the skin. Smooth muscle regulates the pilomoter response, i.e., "goosebumps" via the arector pili muscle.

It is specifically contemplated that a TAARA or any other agonist of smooth muscle contraction known in the art or disclosed herein can be administered to the nipple in combination with an agent that retards systemic absorption of the agent across the dermis. In this manner, agents that might otherwise have unwanted systemic effects can be used to treat nipples while avoiding such systemic side effects. The formulation of agents for topical administration in a manner that avoids systemic absorption is discussed in detail in U.S. 2009/0068287, which is incorporated herein by reference in its entirety.

Other agents that induce contraction of smooth muscle and are specifically contemplated for use to improve the quality of the female sexual experience or in the treatment of FSD are also discussed herein below.

While based in part upon the recognition that the stimulation of contraction of the NAC smooth muscle can erect the nipple, various embodiments include the following.

In one aspect, described herein is a composition for use in improving the female sexual experience or treating FSD, the composition comprising an effective amount of a trace amine associated receptor agonist used to elicit the contraction of the NAC. In one embodiment, the composition is formulated in a topical cream. In one embodiment, the composition is a solution. In one embodiment, the composition is a solution formulated on to a wipe or gauze pad (cotton pad). In one embodiment, the composition is in a form selected from the group consisting of a gel, a foam, an ointment, a lotion, powder, spray, and emulsion. In one embodiment, the trace amine associated receptor agonist is present in the composition in a concentration from about 0.1% to 15% by weight. In one embodiment, the trace amine associated receptor agonist is present in the composition in a concentration from about 0.20% to 30.0% by weight. In one embodiment, the trace amine associated receptor agonist is present in the composition in a concentration of about 0.25% by weight. In one embodiment, the trace amine associated receptor agonist is present in the composition in a concentration of about 0.25%, 0.33%, 0.5%, 1%, 2%, 2.5%, or 10% by weight.

In another aspect, described herein is a composition for use in enhancing sexual satisfaction in a female subject, the composition comprising an effective amount of an trace amine associated receptor agonist used to contract the smooth muscle of the NAC. In one embodiment, the composition is formulated in a topical cream. In one embodiment, the composition is a solution. In one embodiment, the composition is a solution formulated on to a wipe (cotton pad). In one embodiment, the composition is a form selected from the group consisting of a gel, a foam, an ointment, a lotion, powder, spray, and emulsion. In one embodiment, the trace amine associated receptor agonist is present in the composition in a concentration from about 0.1% to 15% by weight. In one embodiment, the trace amine associated receptor agonist is present in the composition in a concentration from about 0.20% to 30.0% by weight. In one embodiment, the trace amine associated receptor agonist is present in the composition in a concentration of about 0.25% by weight. In one embodiment, the trace amine associated receptor agonist is present in the composition in a concentration of about 0.33%, 0.5%, 1%, 2%, or 2.5% by weight.

In another aspect, described herein is a method for improving the female sexual experience or treating FSD in a subject, the method comprising applying an effective amount of a trace amine associated receptor agonist used to contract the smooth muscle of the NAC applied topically to at least a portion of a nipple of the subject. In one embodiment, the trace amine associated receptor agonist is present in the composition in a concentration from about 0.1% to 15% by weight. In one embodiment, the trace amine associated receptor agonist is present in a composition in a concentration from about 0.20% to 30.0% by weight. In one embodiment, the trace amine associated receptor agonist is present in a composition in a concentration of about 0.25% by weight. In one embodiment, the trace amine associated receptor agonist is present in a composition in a concentration of 0.33%, 0.5%, 1%, 2%, or 2.5% by weight. In one embodiment, the trace amine associated receptor agonist is applied to the nipple once daily. In one embodiment, the trace amine associated receptor agonist is applied to the nipple twice daily. In one embodiment, the trace amine associated receptor agonist is applied to the nipple prior to a sexual activity (e.g., foreplay, sexual intercourse or masturbation).

In another aspect, described herein is a method for enhancing sexual satisfaction in a female subject, the method comprising applying an effective amount of an trace amine associated receptor agonist used to contract the smooth muscle of the NAC applied topically to at least a portion of a nipple of the subject. In one embodiment, the trace amine associated receptor agonist is present in the composition in a concentration from about 0.1% to 15% by weight. In one embodiment, the trace amine associated receptor agonist is present in a composition in a concentration from about 0.20% to 30.0% by weight. In one embodiment, the trace amine associated receptor agonist is present in a composition in a concentration of about 0.25% by weight. In one embodiment, the trace amine associated receptor agonist is present in a composition in a concentration of 0.33%, 0.5%, 1%, 2%, or 2.5% by weight. In one embodiment, the trace amine associated receptor agonist is applied to the nipple prior to a sexual activity (e.g., sexual intercourse or masturbation).

In some embodiments of any composition or method involving a trace amine associated receptor agonist, the agonist is octopamine or tyramine. In one embodiment, the octopamine or tyramine is present at a concentration of about 0.1% to 30% by weight.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, can provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention can be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly while operations may be described in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

As used herein, the terms "female sexual dysfunction" or "FSD" refer generally to the impairment of the sexual function in a female. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems. In some embodiments, the FSD is FSAD. In some embodiments, the FSD is HSDD.

As used herein, the terms "male sexual dysfunction" or "MSD" refer generally to the impairment of the sexual function in a male. Sexual dysfunction in males can also include inhibited orgasm. MSD can include erectile dysfunction (difficulty getting and/or keeping an erection), premature ejaculation, delayed or inhibited ejaculation, reaching an orgasm too slowly or not at all, reduced interest in sex, etc.

As used herein, the term "pilomotor effective" refers to an agent or treatment that stimulates contraction of the smooth muscle associated with the pilomotor reflex. A "pilomotor effective amount" of an agent or treatment is an amount sufficient to stimulate contraction of the smooth muscle and stimulate nipple erection.

As used herein, the term "nipple" refers to any portion of the nipple of the female or male breast, including the nipple, the areola, or the "nipple areola complex" (NAC).

As used herein, the term "trace amine associated receptor agonist" refers to a ligand that binds the trace amine associated receptor on smooth muscle cells and activates smooth muscle contraction. Additionally, the term "trace amine associated receptor agonist" can include agents that when applied will induce the release of endogenous trace amine associated receptor agonists (e.g. tyramine) that activates smooth muscle contraction or agents that when applied inhibit the "re-uptake" or degradation of endogenous trace amine associated receptor agonists (e.g. tyramine) that activates smooth muscle contraction. Additionally, the term may refer to a ligand that in addition to binding to the TAAR is a norepinephrine (NE) releasing agent, i.e., known to cause the release of NE, which activates smooth muscle contraction. A "smooth muscle agonist" is an agent that promotes or results in contraction of the smooth muscle including smooth muscle of the nipple, and such agents are specifically contemplated for use in the methods and compositions described herein. Thus, a trace amine associated receptor agonist that promotes or results in smooth muscle contraction is a smooth muscle agonist, but so also are, e.g., an alpha 1 adrenergic receptor agonist or an alpha 2 adrenergic receptor agonist that promotes smooth muscle contraction, agents that that induce the release of endogenous alpha 2 adrenergic receptor agonist that results in smooth muscle contraction, and agents that inhibit the re-uptake or degradation of endogenous alpha 2 adrenergic receptor agonists that activate smooth muscle contraction. For instance, embodiments of the methods disclosed herein can involve application of a composition that will cause erection of the nipple and/or increasing nipple sensitivity via norepinephrine release mediated by a trace amine associated receptor agonist. Other smooth muscle agonists are known in the art and/or discussed herein below (see, e.g., section below headed "Other agents or approaches to contract the smooth muscle.").

As used herein, the terms "treat," "treatment," or "treating" refer to therapeutic treatments, wherein the object is to reverse, alleviate, ameliorate, inhibit, slow down or stop the progression or severity of a disease or condition, e.g., FSD. The term "treating" includes reducing or alleviating at least one adverse effect or symptom of a disease or condition, e.g., FSD. Treatment is generally "effective" if one or more symptoms are reduced. Alternatively, treatment is "effective" if the progression of a disease is reduced or halted. That is, "treatment" includes not just the improvement of symptoms, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality. For example, treatment of FSD is considered effective if the number of satisfying sexual events (SSE) is increased from baseline in a sampled time (e.g. 4 weeks). The term "treatment" of a disease also includes providing relief from the symptoms or side-effects of the disease (including palliative treatment).

The term "statistically significant" or "significantly" refers to statistical significance and generally means a two standard deviation (2SD) or greater difference.

As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs, APHA Acad. Pharm. Sci.* 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech. II,*:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs",Arfv. *Drug Delivery Rev.* 8(1): 1-38 (1992); Fleisher et al. "Improved oral drug delivery: solubility limitations overcome by the use of prodrugs", *Arfv. Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), which are incorporated by reference herein in their entireties.

Other than in the operating examples, or where otherwise indicated, all numbers expressing quantities of ingredients or reaction conditions used herein should be understood as modified in all instances by the term "about." The term "about" when used in connection with percentages can mean ±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

As used herein the term "improvement of the quality of an orgasm and/or enhancement of the quality of sex or the sexual experience" refers to shortening the time required to achieve an orgasm (reducing orgasmic latency), increasing the intensity or duration of an orgasm, increasing the intensity of vaginal contractions during orgasm, increasing vaginal lubrication during intercourse, increasing vaginal discharge, increasing sexual arousal, increasing a feeling of bonding with a sexual partner, increasing oxytocin or prolactin release, increasing sexual desire.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

The technology described herein relates to compositions, methods, and systems for treating FSD and/or enhancing sexual satisfaction in a female subject. In some embodiments, the female subject is a mammal, such as non-human primates (particularly higher primates), sheep, dog, rodent (e.g. mouse or rat), guinea pig, goat, pig, cat, rabbits, cow, and panda. Preferably, the female subject is a human.

Various aspects of the technology described herein involve pilomotor stimulation. Nipple erections are a product of the pilomotor reflex, which causes goose bumps. The measurement or detection of pilomotor stimulation can be performed, at its simplest, by observation of the area at the base of the hair shaft—an agent or treatment that induces arrector pili (i.e., the smooth muscle associated with hair follicle) contraction causes the hair follicle to "stand up" and causes puckering of the skin around the hair shaft commonly referred to as "goose bumps." Thus, if an agent is applied and the hair stands up, goose bumps form, or both, the agent has stimulated the arrector pili (AP). An agent that stimulates the AP muscle would be expected to stimulate contraction in the smooth muscle of the nipple.

Measurement of the strength of AP or nipple smooth muscle contraction can be performed, if necessary, via myograph adapted for that purpose. Examples are described in, e.g., Zeveke & Gladysheva, Bull. Exp. Biol. Med. 71: 102-105 (1971) and Hellmann, J. Physiol. 169: 603-620 (1963), each of which is incorporated herein in its entirety by reference.

Formulations

The therapeutic agents, particularly the TAAR agonists, described herein and used in the present methods may be formulated into compositions according to the knowledge of one of skill in the art. In one embodiment, the TAAR agonist or other stimulator of AP muscle contraction is formulated for topical slow or prolonged release. As but one example, in one embodiment the AP stimulating agent is encapsulated for slow release.

In another embodiment, the composition may comprise an exfoliating agent to promote abrasion of the surface of the nipple. Examples of the exfoliating agent include (1) inorganic and/or metallic particles such as: boron nitride, in body-centered cubic form (Borazon®); aluminosilicate (e.g. nepheline); zircon; mixed oxides of aluminum such as emery; zinc oxide; aluminum oxides such as aluminas or corundum; titanium oxide; titanium oxide coated mica; carbides, in particular silicon carbide (carborundum); or other metal oxides; metals, and metal alloys such as iron shot, steel shot, and in particular perlite; silicates such as glass, quartz, sand, or vermiculite; calcium carbonate (e.g. Bora-Bora sand or Rose de Brignoles sand) or magnesium carbonate; sodium chloride; pumice stone; amorphous silica; diamond; ceramics, and (2) organic particles such as: fruit stones, in particular apricot stones, e.g. Scrubami® apricot; wood cellulose, e.g. ground bamboo stem; coconut shell, e.g. coconut exfoliator; polyamides, in particular Nylon-6; sugars; plastic microbeads, e.g. polyethylenes or polypropylenes; ground walnut; ground apricot seed; ground shells, and (3) mixed particles associating organic and inorganic compounds, and particles coated in the above compounds. The exfoliating agents may be in the form of microbeads of less than five millimeters in its largest dimension that have an exfoliating effect.

In one embodiment, the composition comprising a TAAR agonist can be formulated as a drug. In one embodiment, the composition comprising a TAAR agonist can be formulated as a cosmetic product.

In one embodiment, the composition comprising a TAAR agonists can be formulated as a pharmaceutical or cosmetic agent, which can include formulating the TAAR agonist with any one or combination of abacavir, acebutolol, acetaminophen, acetaminosalol, acetazolamide, acetohydroxamic acid, acetylsalicylic acid, N-acylglutathione ethyl ester and other esters, N-acyl proline ethyl ester and other esters, acitretin, aclovate, acrivastine, actiq, acyclovir, adalimumab, adapalene, adefovir dipivoxil, adenosine, albuterol, alefacept, alfuzosin, allopurinol, alloxanthine, almotriptan, alprazolam, alprenolol, aluminum acetate, aluminum chloride, aluminum chlorohydroxide, aluminum hydroxide, amantadine, amiloride, aminacrine, p-aminobenzoic acid, aminocaproic acid, aminolevulinic acid, aminosalicylic acid, amiodarone, amitriptyline, amlodipine, amocarzine, amodiaquin, amorolfine, amoxapine, amphetamine, ampicillin, anagrelide, anastrozole, anthralin, apomorphine, aprepitant, arbutin, aripiprazole, ascorbic acid, ascorbyl palmitate, atazanavir, atenolol, atomoxetine, atropine, azathioprine, azelaic acid, azelastine, azithromycin, bacitracin, beclomethasone dipropionate, bemegride, benazepril, benzilic acid, bendroflumethiazide, benzocaine, benzonatate, benzophenone, benzoyl peroxide, benztropine, bepridil, betamethasone dipropionate, betamethasone valerate, botulinum toxin, brimonidine, brompheniramine, bupivacaine, buprenorphine, bupropion, burimamide, butenafine, butoconazole, cabergoline, caffeic acid, caffeine, calcipotriene, camphor, candesartan cilexetil, capsaicin, carbamazepine, carbamide peroxide, cefditoren pivoxil, cefepime, cefpodoxime proxetil, celecoxib, cetirizine, cevimeline, chitosan, chlordiazepoxide, chlorhexidine, chloroquine, chlorothiazide, chloroxylenol, chlorpheniramine, chlorpromazine, chlorpropamide, ciclopirox, cilostazol, cimetidine, cinacalcet, ciprofloxacin, citalopram, citric acid, cladribine, clarithromycin, clemastine, clindamycin, clioquinol, clobetasol propionate, clocortolone pivalate, clomiphene, clonidine, clopidogrel, clotrimazole, clozapine, cocaine, codeine, cromolyn, crotamiton, cyclizine, cyclobenzaprine, cycloserine, cytarabine, dacarbazine, dalfopristin, dapsone, daptomycin, daunorubicin, deferoxamine, dehydroepiandrosterone, delavirdine, desipramine, desloratadine, desmopressin, desoximetasone, dexamethasone, dexmedetomidine, dexmethylphenidate, dexrazoxane, dextroamphetamine, diazepam, diclofenac, dicyclomine, didanosine, dihydrocodeine, dihydromorphine, diltiazem, 6,8-dimercaptooctanoic acid (dihydrolipoic acid), diphenhydramine, diphenoxylate, dipyridamole, disopyramide, dobutamine, dofetilide, dolasetron, donepezil, dopa esters, dopamide, dopamine, dorzolamide, doxepin, doxorubicin, doxycycline, doxylamine, doxypin, duloxetine, dyclonine, econazole, efalizumab, eflornithine, eletriptan, emtricitabine, enalapril, ephedrine, epinephrine, epinine, epirubicin, eptifibatide, ergotamine, erythromycin, escitalopram, esmolol, esomeprazole, estazolam, estradiol, etanercept, ethacrynic acid, ethinyl estradiol, ethyl pyruvate, etidocaine, etomidate, famciclovir, famotidine, felodipine, fentanyl, ferulic acid, fexofenadine, finasteride, flecamide, fluconazole, flucytosine, fluocinolone acetonide, fluocinonide, 5-fluorouracil, fluoxetine, fluphenazine, flurazepam, fluticasone propionate, fluvoxamine, formoterol, furosemide, galactarolactone, galactonic acid, galactonolactone, galantamine, gatifloxacin, gefitinib, gemcitabine, gemifloxacin, glucarolactone, gluconic acid, gluconolactone, glucuronic acid, glucuronolactone, glycolic acid, griseofulvin, guaifenesin, guanethidine, N-guanylhistamine, haloperidol, haloprogin, hexylresorcinol, homatropine, homosalate, hydralazine, hydrochlorothiazide, hydrocortisone, hydrocortisone 21-acetate, hydrocortisone 17-butyrate, hydrocortisone 17-valerate, hydrogen peroxide, hydromorphone, hydroquinone, hydroquinone monoether, hydroxyzine, hyoscyamine, hypoxanthine, ibuprofen, ichthammol, idarubicin, imatinib, imipramine, imiquimod, indinavir, indomethacin, infliximab, irbesartan, irinotecan, isoetharine, isoproterenol, itraconazole, kanamycin, ketamine, ketanserin, ketoconazole, ketoprofen, ketotifen, kojic acid, labetalol, lactic acid, lactobionic acid, lamivudine, lamotrigine, lansoprazole, letrozole, leuprolide, levalbuterol, levofloxacin, lidocaine, linezolid, lobeline, loratadine, loperamide, losartan, loxapine, lysergic di ethylamide, mafenide, malic acid, maltobionic acid, mandelic acid, maprotiline, mebendazole, mecamylamine, meclizine, meclocycline, memantine, menthol, meperidine, mepivacaine, mequinol, mercaptopurine, mescaline, metanephrine, metaproterenol, metaraminol, metformin, methadone, methamphetamine, methotrexate, methoxamine, methyldopa esters, methyldopamide, 3,4-methylenedioxymethamphetamine, methyllactic acid, methyl nicotinate, methylphenidate, methyl salicylate, metiamide, metolazone, metoprolol, metronidazole, mexiletine, miconazole, midazolam, midodrine, miglustat, minocycline, minoxidil, mirtazapine, mitoxantrone, moexiprilat, molindone, monobenzone, morphine, moxifloxacin, moxonidine, mupirocin, nadolol, naftifine, nalbuphine, nalmefene, naloxone, naproxen, nefazodone, nelfinavir, neomycin, nevirapine, nicardipine, nicotine, nifedipine, nimodipine, nisoldipine, nitrofurantoin, nizatidine, norepinephrine, nystatin, octopamine, octreotide, octyl methoxycinnamate, octyl salicylate, ofloxacin, olanzapine, olmesartan medoxomil, olopatadine, omeprazole, ondansetron, oxiconazole, oxotremorine, oxybenzone, oxybutynin, oxycodone, oxymetazoline, padimate O, palonosetron, pantothenic acid, pantoyl lactone, paroxetine, pemoline, penciclovir, penicillamine, penicillins, pentazocine, pentobarbital, pentostatin, pentoxifylline, pergolide, perindopril, permethrin, phencyclidine, phenelzine, pheniramine, phenmetrazine, phenobarbital, phenol, phenoxybenzamine, phentolamine, phenylephrine, phenylpropanolamine, phenyloin, N-(phosphonomethyl)-glycine, N-(phosphonomethyl)-creatine, N-(phosphonomethyl)-tyramine, physostigmine, pilocarpine, pimecrolimus, pimozide, pindolol, pioglitazone, pipamazine, piperonyl butoxide, pirenzepine, podofilox, podophyllin, povidone iodine, pramipexole, pramoxine, prazosin, prednisone, prenalterol, prilocalne, procainamide, procaine, procarbazine, praline, promazine, promethazine, promethazine propionate, propafenone, propoxyphene, propranolol, propylthiouracil, protriptyline, pseudoephedrine, pyrethrin, pyrilamine, pyrimethamine, quetiapine, quinapril, quinethazone, quinidine, quinupristin, rabeprazole, reserpine, resorcinol, retinal, 13-cis retinoic acid, retinoic acid, retinol, retinyl acetate, retinyl palmitate, ribavirin, ribonic acid, ribonolactone, rifampin, rifapentine, rifaximin, riluzole, rimantadine, risedronic acid, risperidone, ritodrine, rivastigmine, rizatriptan, ropinirole, ropivacaine, salicylamide, salicylic acid, salmeterol, scopolamine, selegiline, selenium sulfide, serotonin, sertaconazole, sertindole, sertraline, shale tar, sibutramine, sildenafil, sotalol, streptomycin, strychnine, sulconazole, sulfacetamide, sulfabenz, sulfabenzamide, sulfabromomethazine, sulfacetamide (sodium sulfacetamide), sulfachlorpyridazine, sulfacytine, sulfadiazine, sulfadimethoxine, sulfadoxine, sulfaguanole, sulfalene, sulfamethizole, sulfamethoxazole, sulfanilamide, sulfapyrazine, sulfapyridine, sulfasalazine, sulfasomizole, sulfathiazole, sulfisoxazole, sulfur, tacrolimus, tadalafil, tamsulosin, tartaric acid, tazarotene, tegaserol, telithromycin, telmisartan, temozolomide, tenofovir disoproxil, terazosin, terbinafine, terbutaline, terconazole, terfenadine, tetracaine, tetracycline, tetrahydrozoline, thalidomide, theobromine, theophylline, thiabendazole, thioctic acid (lipoic acid), thioridazine, thiothixene, thymol, tiagabine, timolol, tinidazole, tioconazole, tirofiban, tizanidine, tobramycin, tocamide, tolazoline, tolbutamide, tolnaftate, tolterodine, tramadol, tranylcypromine, trazodone, triamcinolone acetonide, triamcinolone diacetate, triamcinolone hexacetonide, triamterene, triazolam, triclosan, triflupromazine, trimethoprim, trimipramine, tripelennamine, triprolidine, tromethamine, tropic acid, tyramine, undecylenic acid, urea, urocanic acid, ursodiol, vardenafil, venlafaxine, verapamil, vitamin E acetate, voriconazole, warfarin, wood tar, xanthine, zafirlukast, zaleplon, zinc pyrithione, ziprasidone, zolmitriptan, and zolpidem.

The amount of therapeutic agent present in the composition may be determined by one of skill in the art using known methodologies. In certain embodiments, the TAAR agonist or other stimulator of AP muscle contraction is present in the composition in a concentration from about 0.20% to 0.30%, or about 0.25% by weight. In another embodiment, the therapeutic agent such as a TAAR agonist is present in the composition in a concentration of about 0.25%, 0.33%, 0.5%, 1%, 2%, 2.5%, or 10% by weight.

In other embodiments, the therapeutic agent, such as the TAAR agonist, is present in the topical composition for use in the methods disclosed herein in a concentration from about 0.1% to 35%, about 1.0% to 30%, about 0.2% to 30%, about 0.2% to 25%, about 0.2% to 20%, about 0.2% to 15%, about 0.2% to 10%, about 0.2% to 5%, about 0.2% to 4%, about 0.2% to 3%, about 0.2% to 2%, about 0.2% to 1%, about 10.0% to 30%, about 15.0% to 30%, about 20.0% to 30%, about 10% to 20%, about 10% to 15%, about 15% to 20%, about 15% to 60%, about 20% to 60%, about 50% to 60%, and about 45% to 55% by weight. For certain therapeutic agents, such as octopamine, or tyramine (racemic mixture), a concentration of about 25% to 60%, 30% to 50%, 30% to 60%, 25% to 30%, 40% to 50%, or 50% to 55% by weight of the total weight of the composition is desirable.

In one embodiment, the composition comprises a TAAR agonist in a concentration of about 0.25%, about 0.33%, about 0.5%, about 1%, about 2%, about 2.5%, about 3.0%, about 4.0%, about 10%, about 15%, about 20%, or about 25% by weight.

The compositions used in the present disclosure, particularly compositions containing a TAAR agonist, may be formulated with a preservative such as EDTA (0.1-0.5% by weight of the formulation) and/or sodium metabisulfite (0.1-0.5% by weight of the formulation). In some embodiments, the penetration enhancer is selected from one or more of the group consisting of alcohols, glycols, fatty acids, fatty esters, fatty ethers, occlusive agents, surface active agents, dimethylaminopropionic acid derivatives, terpenes, sulfoxides, cyclic ethers, amides, and amines. Other components of the formulations used herein may be chosen from cosmetically approved excipients known in the art, including water, thickeners, etc.

It will be understood that the ranges described above, and throughout this document, are also intended to encompass single values contained within these ranges. For example, for a formulation comprising a particular ingredient in a range between 1-50%, a percentage of 5% or 49% is also intended to be disclosed.

A composition for use in the technology described herein can comprise an TAARA in a concentration from about 0.1% to 15% by weight. In one embodiment, the composition comprises a TAARA in a concentration from about 0.1% to 10% by weight. In one embodiment, the composition comprises a TAARA in a concentration from about 0.2% to 15% by weight. In one embodiment, the composition comprises a TAARA in a concentration from about 0.2% to 10% by weight. In one embodiment, the composition comprises a TAARA in a concentration from about 0.2% to 5% by weight. In one embodiment, the composition comprises a TAARA in a concentration from about 0.2% to 4% by weight. In one embodiment, the composition comprises a TAARA in a concentration from about 0.2% to 3% by weight. In one embodiment, the composition comprises a TAARA in a concentration from about 0.2% to 2% by weight. In one embodiment, the composition comprises a TAARA in a concentration from about 0.2% to 1% by weight.

In one embodiment, the composition comprises a TAARA in a concentration of about 0.25% by weight. In one embodiment, the composition comprises a TAARA in a concentration of about 0.33% by weight. In one embodiment, the composition comprises a TAARA in a concentration of about 0.5% by weight. In one embodiment, the composition comprises a TAARA in a concentration of about 1% by weight. In one embodiment, the composition comprises a TAARA in a concentration of about 2% by weight. In one embodiment, the composition comprises a TAARA in a concentration of about 2.5% by weight. In one embodiment, the composition comprises a TAARA in a concentration of about 10% by weight.

In one embodiment, the composition comprising a TAARA can be formulated as a drug. In another embodiment, the composition comprising a TAARA can be formulated as a cosmetic.

The methods of the present disclosure may be used with a TAAR agonist or other compound that causes contraction directly or indirectly of the AP muscle. Suitable TAAR agonists can be utilized including citrus aurantium (e.g. bitter orange extract), 2-phenylethylamine, tyramine, p-tyramine, m-tyramine, N-methyltyramine, tryptamine, octopamine, m-octopamine, p-octopamine, ractopamine, dopamine, 5HT, 3-methoxy-tyramine, trimethylamine, dimethylethylamine, N-methylpiperidine, 3-iodothyronamined, N,N-dimethylcyclohexyl amine, isoamylamine, cycl ohexyl amine, serotonin, 3-methoxytyramine, amphetamine-like, amphetamine, methamphetamine, MDMA, cathinone, methcathinone, phenethylamines, N-methylphenethylamine, 2,5-dimethoxy-4-bromo-phenethylamine, 2,5-dimethoxy-4-propyl-phenethylamine, mescaline, (−)-Ephedrine, tryptamines, psilocin, N,N-dimethyltryptamine, ergolines, lysergic acid diethylamide, piperazines, m-chlorophenylpiperazine, aminoindanes, 2-aminoindane, 5-iodo-2-aminoindane, apomorphine, ractopamine, 3-iodothyronamine, clonidine, guanabenz, idazoxan, RO5073012, RO5166017, RO5203648, RO5256390, RO5263397, RO5212773 (EPPTB), etc. Other suitable TAAR agonists can be found at: Mark D. Berry, et al. Pharmacology of Human Trace Amine-associated Receptors: Therapeutic Opportunities and Challenges. Pharmacology & Therapeutics 18 (2017) 161-180, the entire contents of which is incorporated herein by reference in its entirety. Additionally, derivatives of TAAR agonists can be utilized including derivatives of the compounds mentioned above. In other embodiments, a prodrug that is activated to become a TAAR agonist can be utilized. For example, midodrine is one such prodrug. A particular prodrug can be activated by endogenous enzymes in the scalp such as Caspase-1 when follicular inflammation is present, e.g., at the location of application of a hair extension. In one embodiment, the TAAR agonist is octopamine. In one embodiment, the TAAR is phenyethylamine or octopamine, including compositions comprising the 1-enantiomer of octopamine, that are essentially free of other enantiomers of octopamine, or in which less than 30%, 25%, 20%, 15%, 10%, 12%, 5%, 3%, 1%, or 0.5% by weight of the octopamine present in the composition is a different enantiomer. The octopamine enantiomer R-(−)-4-(2-amino-1-hydroxyethyl)phenol may be obtained from natural bitter orange extract.

In one embodiment of the present invention a topically applied TAAR agonist is selected among : Morpholines, Fenbutrazate, Morazone, Phendimetrazine, Phenmetrazine, Oxazolines, Aminorex, Clominorex, Cyclazodone, Fenozolone, Fluminorex 4-Methylaminorex, Pemoline, Thozalinone, Phenethylamines, 2-OH-PEA, 4-CAB, 4-FA, 4-FMA, 4-MA, 4-MMA, Alfetamine, Amfecloral, Amfepentorex, Amfepramone, Amphetamine, dextroamphetamine, levoamphetamine, Amphetaminil, β-Me-PEA, BDB, Benzphetamine, BOH, Buphedrone, Butylone, Cathine, Cathinone, Clobenzorex, Clortermine, D-Deprenyl, Dim ethyl amphetamine, Dimethylcathinone, dimethylpropion, metamfepramone, DMA, DMMA, EBDB, Ephedrine, Ethcathinone, Ethylamphetamine, Ethylone, Famprofazone, Fenethylline, Fenproporex, Flephedrone, Fludorex, Furfenorex, Hordenine, IAP, IMP, Lisdexamfetamine, Lophophine, MBDB, MDA, tenamfetamine, MDEA, MDMA, MDMPEA, MDOH, MDPEA, Mefenorex, Mephedrone, Mephentermine, Methamphetamine, dextromethamphetamine, levomethamphetamine, Methcathinone, Methedrone, Methylone, NAP, Ortetamine, Paredrine, pBA, pCA, Pentorex, phenpentermine, Phenethylamine, Pholedrine, Phenpromethamine, Phentermine, Phenylpropanolamine, pIA, Prenylamine, Propylamphetamine, Pseudoephedrine, Selegiline, L-deprenyl, Tiflorex, Tyramine, Xylopropamine, Zylofuramine, Piperazines, Benzyl piperazine, BZP, 2,5-Dimethoxy-4-bromobenzylpiperazine, 2C-B-BZP, Methylbenzylpiperazine, MBZP, Metachlorophenylpiperazine, mCPP, Methylenedioxybenzylpiperazine, MDBZP, Methoxyphenylpiperazine, MeOPP, Parafluorophenylpiperazine, pFPP, 2-Amino-1,2-dihydronaphthalene, 2-Aminoindane, 2-Aminotetralin, 2-Benzylpiperidine, 4-Benzylpiperidine, Clofenciclan, Cyclopentamine, Cypenamine, Cyprodenate, Feprosidnine, Gilutensin, Heptaminol, Hexacyclonate, Indanorex, 5-Iodo-2-aminoindane, 5-IAI, Isometheptene, Methylhexanamine, Octodrine, Phthalimidopropiophenone, Propylhexedrine, levopropylhexedrine, Tuaminoheptane.

In one embodiment, the TAAR agonist is tyramine, or a pharmaceutically acceptable salt or hydrate thereof. Other agents can be 4-(2-Aminoethyl)phenol, 51-67-2, 4-Hydroxyphenethyl amine, P-Tyramine, 2-(4-Hydroxyphenyl) ethyl amine, Hydroxyphenethylamine, 4-(2-Aminoethyl) phenol, 4-Hydroxyphenethylamine, p-Tyramine, para-Tyramine, Tyramine, 4-(2-Aminoethyl)phenol, 51-67-2, 4-Hydroxyphenethylamine, p-Tyramine, 2-(4-Hydroxyphenyl)ethylamine, Uteramine, Tyramin, Tyrosamine, Tocosine, 4-Hydroxyphenylethylamine, Systogene, Phenol, 4-(2-aminoethyl)-p-Hydroxyphenethylamine, Tenosin-wirkstoff, p-Hydroxyphenylethylamine, p-(2-Aminoethyl)phenol, 2-(p-Hydroxyphenyl)ethylamine, Phenethylamine, p-hydroxy-p-beta-Aminoethylphenol, Phenol, p-(2-aminoethyl)-Benzeneethanamine, 4-hydroxy-Tyramine base, beta-Hydroxyphenylethylamine, NSC 249188, alpha-(4-Hydroxyphenyl)-beta-aminoethane, UNII-X8ZC7V0OX3, [3H]tyramine, [3H]-Tyramine, BRN 1099914, etc.

In one embodiment, the TAAR agonist is octopamine or tyramine, or a pharmaceutically acceptable salt or hydrate thereof, in a composition in a concentration of 0.25% to 40%, 0.25% to 25% by weight, or 0.5% to 22.5% by weight, or 0.75% to 20% by weight, or 1% to 17.5% by weight, or 1.5% to 15% by weight, or 2% to 14.5% by weight, or 2.5% to 14% by weight, or 5% to 13.5% by weight, or 7.5% to 12.5% by weight, or 8% to 12% by weight, or 8.5% to 11.5% by weight, or 9% to 11% by weight, or 9.25% to 10.75% by weight, or 9.5% to 10.5% by weight, or 9.6% to 10.4% by weight, or 9.7% to 10.3% by weight, or 9.8% to 10.2% by weight, or 9.9% to 10.1% by weight, or 9.95% to 10.05% by weight, or 9.96% to 10.04% by weight, or 9.97% to 10.03% by weight, or 9.98% to 10.02% by weight, or 9.99% to 10.01% by weight.

In one embodiment, the TAAR agonist is octopamine or tyramine, or a pharmaceutically acceptable salt or hydrate thereof, in a composition in a concentration at a range of 0.25%, 0.5%, 0.75%, 1%, 1.5%, 2%, 2.5%, 5%, 7.5%, 8%, 8.5%, 9%, 9.25%, 9.5%, 9.6%, 9.7%, 9.8%, 9.9%, 9.95%, 9.96%, 9.97%, 9.98%, or 9.99% by weight as the lower weight limit of the range to an upper weight limit of 10.01%, 10.02%, 10.03%, 10.04%, 10.05%, 10.1%, 10.2%, 10.3%, 10.4%, 10.5%, 10.75%, 11%, 11.5%, 12%, 12.5%, 13.5%, 14%, 14.5%, 15%, 17.5%, 20%, 22.5%, 25%, 30%, 35%, 40%, 45%, or 50% by weight (e.g., a range of 0.25% to 10.01%, 0.25% to 10.02%, 0.5% to 10.01%, 0.5% to 10.02%, etc.).

In one embodiment, the TAAR agonist is octopamine or tyramine, or a pharmaceutically acceptable salt or hydrate thereof, in a composition in a concentration of 0.25% by weight, or 0.5% by weight, or 0.75% by weight, or 1% by weight, or 1.5% by weight, or 2% by weight, or 2.5% by weight, or 5% by weight, or 7.5% by weight, or 8% by weight, or 8.5% by weight, or 9% by weight, or 9.25% by weight, or 9.5% by weight, or 9.6% by weight, or 9.7% by weight, or 9.8% by weight, or 9.9% by weight, or 9.95% by weight, or 9.96% by weight, or 9.97% by weight, or 9.98% by weight, or 9.99% by weight, or 10% by weight, or 10.01% by weight, or 10.02% by weight, or 10.03% by weight, or 10.04% by weight, or 10.05% by weight, or 10.1% by weight, or 10.2% by weight, or 10.3% by weight, or 10.4% by weight, or 10.5% by weight, or 10.75% by weight, or 11% by weight, or 11.5% by weight, or 12% by weight, or 12.5% by weight, or 13.5% by weight, or 14% by weight, or 14.5% by weight, or 15% by weight, or 17.5% by weight, or 20% by weight, or 22.5% by weight, or 25% by weight, or 30% by weight, or 40% by weight, or 45% by weight, or 50% by weight, or 55% by weight.

In another embodiment, the composition comprises a TAAR agonist that is octopamine or tyramine, or a pharmaceutically acceptable salt or hydrate thereof, or that comprises one enantiomer of octopamine or tyramine, namely R-(−)-4-(2-amino-1-hydroxyethyl)phenol and is substantially free of other enantiomer(s) of octopamine or has less than 30%, 25%, 20%, 15%, 10%, 12%, 5%, 3%, 1%, or 0.5% by weight of the octopamine or tyramine present in the composition as a different enantiomer, wherein the octopamine or tyramine is present in the composition in a concentration of 30% to 70% by weight, or 35% to 65% by weight, or 37.5% to 62.5% by weight, or 40% to 60% by weight, or 42.5% to 57.5% by weight, or 45% to 55% by weight, or 45.5% to 54.5% by weight, or 46% to 54% by weight, or 46.5% to 53.5% by weight, or 47% to 53% by weight, or 47.5% to 52.5% by weight, or 48% to 52% by weight, or 48.25% to 51.75% by weight, or 48.5% to 51.5% by weight, or 48.75% to 51.25% by weight, or 49% to 51% by weight, or 49.25% to 50.75% by weight, or 49.5% to 50.5% by weight, or 49.6% to 50.4% by weight, or 49.7% to 50.3% by weight, or 49.8% to 50.2% by weight, or 49.9% to 50.1% by weight.

In another embodiment, the composition comprises a TAAR agonist that is octopamine or tyramine, or a pharmaceutically acceptable salt or hydrate thereof, or that comprises one enantiomer of octopamine or tyramine, namely R-(−)-4-(2-amino-1-hydroxyethyl)phenol and is substantially free of other enantiomer(s) of octopamine or tyramine or has less than 30%, 25%, 20%, 15%, 10%, 12%, 5%, 3%, 1%, or 0.5% by weight of the octopamine present in the composition as a different enantiomer, wherein the octopamine or tyramine is present in the composition in a concentration of 20% by weight, or 25% by weight, or 30% by weight, or 35% by weight, or 37.5% by weight, or 40% by weight, or 42.5% by weight, or 45% by weight, or 45.5% by weight, or 46% by weight, or 46.5% by weight, or 47% by weight, or 47.5% by weight, or 48% by weight, or 48.25% by weight, or 48.5% by weight, or 48.75% by weight, or 49% by weight, or 49.25% by weight, or 49.5% by weight, or 49.6% by weight, or 49.7% by weight, or 49.8% by weight, or 49.9% by weight to 50.1% by weight, or 50.2% by weight, or 50.3% by weight, or 50.4% by weight, or 50.5% by weight, or 50.75% by weight, or 51% by weight, or 51.25% by weight, or 51.5% by weight, or 51.75% by weight, or 52% by weight, or 52.5% by weight, or 53% by weight, or 53.5% by weight, or 54% by weight, or 54.5% by weight, or 55% by weight, or 57.5% by weight, or 60% by weight, or 62.5% by weight, or 65% by weight, or 70% by weight.

In one embodiment, the composition comprises a TAAR agonist that is R-(−)-4-(2-amino-1-hydroxyethyl)phenol substantially free of the other enantiomer of octopamine or tyramine (or having less than 25%, 20%, 15%, 10%, 5%, 1% or 0.1% of the other enantiomer of octopamine or tyramine) or a pharmaceutically acceptable salt or hydrate thereof, in a composition in a concentration of 20% by weight, or 21% by weight, or 25% by weight, or 26% by weight, or 30% by weight, or 35% by weight, or 37.5% by weight, or 40% by weight, or 42.5% by weight, or 45% by weight, or 45.5% by weight, or 46% by weight, or 46.5% by weight, or 47% by weight, or 47.5% by weight, or 48% by weight, or 48.25% by weight, or 48.5% by weight, 48.75% by weight, or 49% by weight, or 49.25% by weight, or 49.5% by weight, or 49.6% by weight, or 49.7% by weight, or 49.8% by weight, or 49.9% by weight, or 50% by weight, or 50.1% by weight, or 50.2% by weight, or 50.3% by weight, or 50.4% by weight, or 50.5% by weight, or 50.75% by weight, or 51% by weight, or 51.25% by weight, or 51.5% by weight, or 51.75% by weight, or 52% by weight, or 52.5% by weight, or 53% by weight, or 53.5% by weight, or 54% by weight, or 54.5% by weight, or 55% by weight, or 57.5% by weight, or 60% by weight, or 62.5% by weight, or 65% by weight, or 70% by weight.

In another embodiment, the composition comprises a TAAR agonist that is octopamine or tyramine, or a pharmaceutically acceptable salt or hydrate thereof, or that comprises one enantiomer of octopamine or tyramine, namely R-(−)-4-(2-amino-1-hydroxyethyl)phenol and is substantially free of other enantiomer(s) of octopamine or tyramine or has less than 30%, 25%, 20%, 15%, 10%, 12%, 5%, 3%, 1%, or 0.5% by weight of the octopamine present in the composition as a different enantiomer, wherein the octopamine or tyramine is present in the composition in a concentration of 10% to 60% by weight, or 12.5% to 50% by weight, or 10% to 50% by weight, or 15% to 40% by weight, or 20% to 30% by weight, or 20% to 40% by weight, or 17.5% to 30% by weight, or 20% to 25% by weight, or 20.5% to 24.5% by weight, or 21% to 24% by weight, or 21.5% to 23.5% by weight, or 21.75% to 23.25% by weight, or 22% to 23% by weight, or 22.1% to 22.9% by weight, or 22.2% to 22.8% by weight, or 22.3% to 22.7% by weight, or 22.4% to 22.6% by weight.

In another embodiment, the composition comprises a TAAR agonist that is octopamine or tyramine, or a pharmaceutically acceptable salt or hydrate thereof, or that comprises one enantiomer of octopamine or tyramine, namely R-(−)-4-(2-amino-1-hydroxyethyl)phenol and is substantially free of other enantiomer(s) of octopamine or tyramine or has less than 30%, 25%, 20%, 15%, 10%, 12%, 5%, 3%, 1%, or 0.5% by weight of the octopamine present in the composition as a different enantiomer, wherein the octopamine or tyramine is present in the composition in a concentration of 10% by weight, or 12.5% by weight, or 15% by weight, or 17.5% by weight, or 20% by weight, or 20.5% by weight, or 21% by weight, or 21.5% by weight, or 21.75% by weight, or 22% by weight, or 22.1% by weight, or 22.2% by weight, or 22.3% by weight, or 22.4% by weight to 22.6% by weight, or 22.7% by weight, or 22.8% by weight, or 22.9% by weight, or 23% by weight, or 23.25% by weight, or 23.5% by weight, or 24% by weight, or 24.5% by weight, or 25% by weight, or 30% by weight, or 40% by weight, or 50% by weight, or 60% by weight.

In one embodiment, the composition comprises one enantiomer of octopamine, namely R-(−)-4-(2-amino-1-hydroxyethyl)phenol, and is substantially free of other enantiomer(s) of octopamine or tyramine or has less than 30%, 25%, 20%, 15%, 10%, 12%, 5%, 3%, 1%, or 0.5% by weight of the octopamine or tyramine present in the composition as a different enantiomer, wherein the R-(−)-4-(2-amino-1-hydroxyethyl)phenol is present in the composition in a concentration of 20% to 25% by weight.

In a further embodiment, the TAAR agonist is phenylethylamine, or a pharmaceutically acceptable salt or hydrate thereof, in a composition in a concentration of 0.01% to 2% by weight, or 0.02% to 1.75% by weight, or 0.03% to 1.5% by weight, or 0.04% to 1.25% by weight, or 0.05% to 1% by weight, or 0.1% to 0.9% by weight, or 0.15% to 0.85% by weight, or 0.2% to 0.8% by weight, or 0.25% to 0.75% by weight, or 0.3% to 0.7% by weight, or 0.35% to 0.65% by weight, or 0.4% to 0.6% by weight, or 0.41% to 0.59% by weight, or 0.42% to 0.58% by weight, or 0.43% to 0.57% by weight, or 0.44% to 0.56% by weight, or 0.45% to 0.55% by weight, or 0.46% to 0.54% by weight, or 0.47% to 0.53% by weight, or 0.48% to 0.52% by weight, or 0.49% to 0.51% by weight.

In a further embodiment, the TAAR agonist is phenylethylamine, or a pharmaceutically acceptable salt or hydrate thereof, in a composition in a concentration of 0.01% by weight, or 0.02% by weight, or 0.03% by weight, or 0.04% by weight, or 0.05% by weight, or 0.1% by weight, or 0.15% by weight, or 0.2% by weight, or 0.25% by weight, or 0.3% by weight, or 0.35% by weight, or 0.4% by weight, or 0.41% by weight, or 0.42% by weight, or 0.43% by weight, or 0.44% by weight, or 0.45% by weight, or 0.46% by weight, or 0.47% by weight, or 0.48% by weight, or 0.49% by weight to 0.51% by weight, or 0.52% by weight, or 0.53% by weight, or 0.54% by weight, or 0.55% by weight, or 0.56% by weight, or 0.57% by weight, or 0.58% by weight, or 0.59% by weight, or 0.6% by weight, or 0.65% by weight, or 0.7% by weight, or 0.75% by weight, or 0.8% by weight, or 0.85% by weight, or 0.9% by weight, or 1% by weight, or 1.25% by weight, or 1.5% by weight, or 1.75% by weight, or 2% by weight.

In a further embodiment, the TAAR is phenylethylamine, or a pharmaceutically acceptable salt or hydrate thereof, in a composition in a concentration of 0.01% by weight, or 0.02% by weight, or 0.03% by weight, or 0.04% by weight, or 0.05% by weight, or 0.1% by weight, or 0.15% by weight, or 0.2% by weight, or 0.25% by weight, or 0.3% by weight, or 0.35% by weight, or 0.4% by weight, or 0.41% by weight, or 0.42% by weight, or 0.43% by weight, or 0.44% by weight, or 0.45% by weight, or 0.46% by weight, or 0.47% by weight, or 0.48% by weight, or 0.49% by weight, or 0.5% by weight, or 0.51% by weight, or 0.52% by weight, or 0.53% by weight, or 0.54% by weight, or 0.55% by weight, or 0.56% by weight, or 0.57% by weight, or 0.58% by weight, or 0.59% by weight, or 0.6% by weight, or 0.65% by weight, or 0.7% by weight, or 0.75% by weight, or 0.8% by weight, or 0.85% by weight, or 0.9% by weight, or 1% by weight, or 1.25% by weight, or 1.5% by weight, or 1.75% by weight, or 2% by weight.

In some embodiments, provided herein is a TAAR agonist formulated with a carrier or delivery vehicle optimized for delivery of the TAAR agonist to the nipple. A TAAR agonist can be released using several different formulations or release methods including time release, creams, ointments, sprays, capsules, or other release methods. For instance the TAAR agonist can be included in ointments or other topical creams that could be applied to the nipple so that it can be slowly absorbed into the skin and stimulate the smooth muscle. In other embodiments, the TAAR agonist can be included in a liquid spray or aerosol medium to be applied to the nipple. In other embodiments, the TAAR agonist can be incorporated into capsules or other slow release vehicles that would allow the chemical or agent to be slowly released into the dermis of the nipple. Capsules or vehicles that encapsulate the TAAR agonist can include, but are not limited to, liposomes, non-ionic liposomes, niosomes, novasome I, erythromycin-Zn complex, microspheres, nanoparticles, solid lipid nanoparticles, and nanoemulsions. In some embodiments, this can include a gel or foam that is applied to the nipple. It is specifically contemplated that the TAAR agonist can be formulated in a solution soaked onto a wetted gauze pad.

Agents that promote the contraction of the AP muscle can optionally be administered by iontophoresis, which uses an electric field to drive the passage of ionic agents or drugs into the skin. As but one example, iontophoresis has been used to deliver agents such as phenylephrine to the skin to stimulate AP muscle contraction (See, e.g., Siepmann et al., Neurology Apr. 25, 2012; 78(Meeting Abstracts 1): P05.197). Thus, in one embodiment, a brush or comb can incorporate an iontophoresis device, which can dispense the TAARA or other agent and/or be used for transdermal delivery of the agent(s). The iontophoresis device can comprise one or more metal contacts. Optionally, the iontophoresis device can comprise one or more compartments for containing the TAAR agonist or other agent(s).

Other Agents or Approaches to Contract the Smooth Muscle

Other agents or approaches can be used to erect the nipple and increase sensitivity of the breast for treatment of FSD or to increase the quality of the female sexual experience. As noted above, any agent or treatment that stimulates AP muscle contraction is of potential use in methods of treating, reducing or preventing FSD or to increase the quality of the female sexual experience as described herein. Any of these methods can be used in combination with the TAAR induced muscle contraction described previously.

In one embodiment, the smooth muscle can be contracted by stimulating or activating a cold receptor. A cold receptor can be stimulated, for example, by activating the TRPM8 channel. Exemplary agents that can stimulate a cold receptor include, but are not limited to, menthol and icilin. Compositions and methods for stimulating a cold receptor are disclosed, for example, in U.S. Pat. No. 4,034,109, the contents of which are incorporated by reference in its entirety.

Where the AP muscle is served by or associated with both noradrenergic fibers and a cholinergic system, agents that stimulate release of transmitters from these systems can be used to stimulate AP muscle contraction. Thus, not only TAAR agonists, but also cholinergic agonists, including, but not limited to acetylcholine and other neurotransmitters that stimulate smooth muscle contraction are contemplated for use in the methods and compositions described herein.

The alpha 1 adrenergic receptor is a G protein-coupled receptor. Agonists of other G protein-coupled receptors (e.g., alpha 2 adrenergic receptor) can also be used to stimulate contraction of the smooth muscle. Examples of alpha 2 adrenergic receptor agonists include, but are not limited to, 4-NEMD, 7-Me-marsanidine, agmatine, apraclonidine, brimonidine, clonidine, detomidine, dexmedetomidine, fadolmidine, guanabenz, guanfacine, lofexidine, marsanidine, medetomidine, methamphetamine, mivazerol, rilmenidine, romifidine, talipexole, tizanidine, tolonidine, xylazine, and xylometazoline. As noted above, to the extent that it would be disadvantageous to administer these or other agents systemically, they can be administered in a formulation that permits uptake by the AP muscle in the dermis but limits systemic uptake.

In one embodiment of the present invention a TAAR agonist may be combined with a topically applied alpha adrenergic receptor agonist. Suitable alpha agonists can include cirazoline, desvenlafaxine, etilfrine, metaraminol, methoxamine, naphazoline, oxymetazoline, pseudoephrine, m-synephrine, p-synephrine, synephrine, octopamine, hordenine, tetrahydrozoline, isometheptene, metaraminol, nicergoline, ergonovine, levonordefrin, phendimetrazine, methoxamine, midodrine, clonidine, pergolide, xylometazoline, droxidopa, epinephrine, mephentermine, 4-methoxyamphetamine, Benzphetamine, Naphazoline, Apraclondine, Bromocriptine, Oxymetazoline, Phenylpropanolamine, Pseudoephedrine, Dipivefrin, xylometazoline, etc. Additionally, derivatives of alpha 1 receptor agonists can be utilized including derivatives of the compounds mentioned above. In other embodiments, a prodrug that is activated to become an alpha 1 receptor agonist can be utilized. For example, midodrine is one such prodrug. A particular prodrug can be activated by endogenous enzymes in the skin such as Caspase-1.

In one embodiment of the present invention a TAAR agonist may be combined with a topically applied alpha adrenergic receptor antagonist. Suitable alpha antagonists can include (+)Dobutamine, abanoquil, Acebutolol, adimolol, ajmalicine, alfuzosin, anisodamine, Atenolol, benoxathian, Betaxolol, Bretylium, Buflomedil, Butoxamine, Carteolol, carvedilol, cirazoline, corynanthine, dihydroergocornine, dihydroergocristine, dihydroergocryptine, dihydroergotoxine, doxazosin , ergot derivatives, Esmolol, Guanadrel, Guanethidine, hydroxymaprotiline, ifenprodil, indoramin, ketanserin, labetalol, Levobunolol, Metoprolol, monatepil, Moxisylyte, Nadolol, nantenine, Nicergoline, oxaprotiline, pelanserin, Penbutolol, phendioxan, phenoxybenzamine, phentolamine, Pindolol, prazosin , Propanolol, pukateine, Raubasine, rauwolscine, Reserpine, silodosin, tamsulosin, terazosin , thiamenidine, tiamenidine, Timolol, Tolazoline, umespirone, urapidil, urapidil, WB-4101, yohimbine, ziprasidone, zuclopenthixol, L-765, 314, Z-350, SR 59230A, BMY-7,378.

In one embodiment of the present invention, a TAAR agonist may be combined with a topically applied norepinephrine (NE) re-uptake inhibitor. In one embodiment a TAAR agonist that is a NE releasing agent may be combined with a topically applied norepinephrine (NE) re-uptake inhibitor. Suitable NE re-uptake inhibitors can include Amedalin, Atomoxetine, tomoxetine, Ciclazindol, Daledalin, Esreboxetine, Lortalamine, Mazindol, Nisoxetine, Reboxetine, Talopram, Talsupram, Tandamine, Viloxazine, Amineptine, Bupropion, amfebutamone, Fencamine, Fencamfamine, Lefetamine, Levophacetoperane, LR-5182, Manifaxine, Methylphenidate, Nomifensine, O-2172, Radafaxine, Bicifadine, Desvenlafaxine, Duloxetine, Eclanamine, Levomilnacipran, Milnacipran, Sibutramine, Venlafaxine, Brasofensine, Diclofensine, DOV-102,677, DOV-21, 947, DOV-216,303, JNJ-7925476, JZ-IV-10, Methylnaphthidate, Naphyrone, NS-2359, PRC200-SS, SEP-225,289, SEP-227,162, Tesofensine, Amitriptyline, Butriptyline, Cianopramine, Clomipramine, Desipramine, Dosulepin, Doxepin, Imipramine, Lofepramine, melitracen, Nortriptyline, Protriptyline, Trimipramine, Amoxapine, Maprotiline, Mianserin, Oxaprotiline, Setiptiline, Cocaine, CP-39,332, EXP-561, Fezolamine, Ginkgo biloba, Indeloxazine, Nefazodone, Nefopam, Pridefrine, Tapentadol, Teniloxazine, Tramadol, Ziprasidone.

In one embodiment of the present invention a TAAR agonist may be combined with a topically applied beta adrenergic receptor agonist.

In one embodiment of the present invention a TAAR agonist may be combined with a topically applied beta adrenergic receptor antagonist.

In one embodiment of the present invention a TAAR agonist may be combined with a topically applied monoamine oxidase (MAO) and/or Catechol-O-methyltransferase (COMT) inducer or activator thereby increasing the MAO and/or COMT degradation rate of the TAAR agonist.

In one embodiment of the present invention a TAAR agonist may be combined with a topically applied monoamine oxidase (MAO) and/or Catechol-O-methyltransferase (COMT) inhibitor thereby decreasing the MAO and/or COMT degradation rate of the TAAR agonist.

In one embodiment, halostachine (also known as N-methylphenylethanolamine) is contemplated for use as a therapeutic agent in the methods and compositions described herein to stimulate smooth muscle contraction.

It should be noted that agonists described herein also encompass their inorganic or organic salts. Representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

It should be noted that combinations of the above methods and agents can be used to promote the contraction of the smooth muscle.

It should be noted that combinations of the above methods with an applied TAAR agonist and agents can be used to promote the contraction of the smooth muscle.

In some embodiments, provided herein is a TAARA formulated with a carrier or delivery vehicle optimized for delivery of the TAARA to the nipple. The trace amine associated receptor agonist ("TAARA") can be released using several different formulations or release methods including time release, creams, ointments, sprays, capsules, or other release methods. In other embodiments, the TAARA can be included in ointments or other topical creams that could be applied to the nipple so that it can be slowly absorbed into the skin and stimulate the smooth muscle. In other embodiments, the TAARA can be included in a liquid spray or aerosol medium to be applied to the nipple. In other embodiments, the TAARA can be incorporated into capsules or other slow release vehicles that would allow the chemical or agent to be slowly released into the dermis. Capsules or vehicles that encapsulate the TAARA can include, but are not limited to, liposomes, non-ionic liposomes, niosomes, novasome I, erythromycin-Zn complex, microspheres, nanoparticles, solid lipid nanoparticles, and nanoemulsions. In some embodiments, this can include a gel or foam that is applied to the skin. In some embodiments, this can include a solution packaged with a piece of gauze or cotton pad.

In some embodiments, the compositions can further comprise a flavoring agent. One example of the flavoring agent is a sweetening agent.

In some embodiments, the composition described herein is applied to the nipple once daily. In one embodiment, the composition described herein is applied to the nipple twice daily. In one embodiment, the composition described herein is applied to the skin prior to a sexual activity. Examples of sexual activities include, but are not limited to, foreplay, sexual intercourse, and masturbation.

Efficacy of treatment for FSD can be determined by monitoring the number of satisfying sexual events (SSE) in a given experimental period. For example, a questionnaire may be administered by a clinician asking the number of SSEs a patient has experienced in a given four-week period. A treatment can thus be applied for another four-week period and the questionnaire can be re-assessed at the end of the treatment. An increase in SSE from baseline can then be evaluated, for example, in a statistically significantly large cohort. As but one example, an average increase from 6 to 6.7 SSEs would show efficacy of a treatment. Similarly, secondary endpoints could include questionnaires assessing sexual satisfaction, e.g., change from baseline to end-of-study in arousal domain score, female sexual function index, satisfaction with arousal, desire domain from female sexual function index, satisfaction with desire, quality of relationship with partner, and a female sexual distress scale.

Agents that promote the contraction of smooth muscle can optionally be administered by iontophoresis, which uses an electric field to drive the passage of ionic agents or drugs into the skin. As but one example, iontophoresis has been used to deliver agents such as phenylephrine to the skin to stimulate nipple smooth muscle contraction (See, e.g., Siepmann et al., Neurology Apr. 25, 2012; 78(Meeting Abstracts 1): P05.197). Thus, in one embodiment, a device can incorporate an iontophoresis device, which can dispense the TAARA or other agent and/or be used for transdermal delivery of the agent(s). The iontophoresis device can comprise one or more metal contacts. Optionally, the iontophoresis device can comprise one or more compartments for containing the TAARA or other agent(s).

Generating Trace Amine Via Local Flora

It is contemplated for some embodiments to include the use of an agent that can induce local flora to generate trace amine. For example, an agent such as a probiotic, a genetically modified (GMO) bacteria, or a viral vector can be used to induce local flora in a person in need of treatment so as to cause generation of a TAAR. Using an agent to induce the generation of TAAR can be done instead of applying a topical composition containing a TAAR agonist or in addition to applying the topical composition containing the TAAR agonist.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein.

Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, any processes described or depicted herein do not necessarily require the particular order described or shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that can have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

EXAMPLES

Example 1

A pilot study was conducted to assess the dosage of topical tyramine hydrochloride solution required to elicit nipple erection and increased nipple sensitivity. Five subjects ages 18-70 participated in the study. Two subjects were post-menopausal and the reminder three were pre-menopausal. Subjects were not hypertensive, pregnant or breast-feeding. Three formulations were used: Formula A: 0% topical tyramine hydrochloride solution; Formula B: 5% topical tyramine hydrochloride solution; Formula C: 10% topical tyramine hydrochloride solution.

The study was conducted over 3 days. On day 1, subjects were instructed to apply on the left nipple Formula A and on the right nipple Formula B. On day 2, subjects were instructed to apply on the left nipple Formula A and on the right nipple Formula C. On day 3, subjects were instructed to apply on the left nipple Formula B and on the right nipple Formula C. 0.1 mL of each formula was applied with a cotton swab to the nipple areole complex. Table 1 summarizes the finding from this study. The 10% topical tyramine solution (Formula C) elicited a clinical response in all subjects while the 5% and placebo formulations (Formula A and B) failed to elicit a response. With the 10% topical tyramine solution, response in nipple erection and increased nipple sensitivity was obtained in less than 20 minutes and lasted for 3-4 hours. The results illustrate an important proof of concept, because tyramine is a selective TAAR agonist and would not erect the nipple via andrenergic (alpha or beta) mechanisms.

TABLE 1

| Subject Nr. | Day 1 | | Day 2 | | Day 3 | |
|---|---|---|---|---|---|---|
| | Formula A | Formula B | Formula A | Formula C | Formula B | Formula C |
| 001 | NR | NR | NR | R | NR | R |
| 002 | NR | NR | NR | R | NR | R |
| 003 | NR | NR | NR | R | NR | R |
| 004 | NR | NR | NR | R | NR | R |
| 005 | NR | NR | NR | R | NR | R |

R = Response i.e., nipple erection
NR = No Response

Example 2

An additional pilot study was conducted to assess the efficacy of topical tyramine applied to the nipple-areole complex to improve the quality of the female sexual experience. Nine women subjects ages 18-70 participated in the study. Two subjects were post-menopausal and the remaining seven were pre-menopausal. Subjects were not suffering from clinical depression, hypertension, pregnant, breast-feeding or currently taking testosterone, SSRIs, or other antidepressants. ~1.0 mL of 10% topical tyramine hydrochloride solution was given to subjects in the form of 12 pre-wetted gauze pads individually sealed in a pouch. Subjects were instructed to apply one pad to both nipples ~1 hour before sexual activity. The duration of the study was for a period of two weeks. The number of Satisfying Sexual Events (SSE) determined by a Sexual Activity Record (SAR) was recorded. In addition, a modified Female Sexual Function Index (FSFI) desire domain questionnaire was administered. Table 2 summarizes the change in SSEs from baseline. All subjects reported increased nipple sensitivity within 30 minutes after the application of the topical tyramine solution. The nipples remained sensitive up to 3 to 4 hours. Six subjects reported change in the number of SSEs from baseline. Subjects reporting increase in the number of SSEs also reported increased desire possibly attributed to the hypothesized mechanism of action of oxytocin release as a result of nipple erection.

TABLE 2

| Subject Nr. | Number of SSE (baseline) | Number of SSE (1 week) |
|---|---|---|
| 001 | 1 | 3 |
| 002 | 0 | 2 |
| 003 | 0 | 1 |
| 004 | 2 | 2 |
| 005 | 1 | 3 |
| 006 | 2 | 2 |
| 007 | 1 | 1 |
| 008 | 3 | 6 |
| 009 | 2 | 3 |

Example 3

A pilot study was conducted to assess the dosage of topical octopamine hydrochloride solution required to elicit nipple erection and increase nipple sensitivity. Five subjects ages 18-70 participated in the study. Two subjects were post-menopausal and the reminder three were pre-menopausal. Subjects were not hypertensive, pregnant or breast-feeding. Three formulations were used: Formula A: 0% topical octopamine hydrochloride solution; Formula B: 10% topical octopamine hydrochloride solution; Formula C: 20% topical octopamine hydrochloride solution.

The study was conducted over 3 days. On day 1, subjects were instructed to apply on the left nipple Formula A and on the right nipple Formula B. On day 2, subjects were instructed to apply on the left nipple Formula A and on the right nipple Formula C. On day 3, subjects were instructed to apply on the left nipple Formula B and on the right nipple Formula C. 0.1 mL of each formula was applied with a cotton swab to the nipple areole complex. Table 3 summarizes the finding from this study. The 20% topical octopamine solution (Formula C) elicited a clinical response in all subjects while the 10% and placebo formulations (Formula A and B) failed to elicit a response. With the 20% topical octopamine solution, response in nipple erection and sensitivity was obtained in less than 20 minutes and lasted for 3-4 hours. The results illustrate the use of an alpha 1 and TAAR receptor agonist, as octopamine binds both alpha 1 adrenergic receptors and TAARs. This is advantageous because some subjects may not express significant alpha 1 adrenergic receptors in the NAC to elicit a response but will be stimulated with TAAR agonist. Conversely, a subject may be deficient in TAARs but have sufficient alpha 1 adrenergic receptors to stimulate nipple erection with the agent.

TABLE 3

| Subject Nr. | Day 1 Formula A | Day 1 Formula B | Day 2 Formula A | Day 2 Formula C | Day 3 Formula B | Day 3 Formula C |
|---|---|---|---|---|---|---|
| 001 | NR | NR | NR | R | NR | R |
| 002 | NR | NR | NR | R | NR | R |
| 003 | NR | NR | NR | R | NR | R |
| 004 | NR | NR | NR | R | NR | R |
| 005 | NR | NR | NR | R | NR | R |

R = Response i.e., nipple erection
NR = No Response

Example 4

An additional pilot study was conducted to assess the efficacy of topical octopamine applied to the nipple-areole complex to improve the quality of the female sexual experience. Nine women subjects ages 18-70 participated in the study. Two subjects were post-menopausal and the remaining seven were pre-menopausal. Subjects were not suffering from clinical depression, hypertension, pregnant, breast-feeding or currently taking testosterone, SSRIs, or other antidepressants. ~1.0 of 20% topical octopamine hydrochloride solution was provided to each subject on pre-wetted guaze pads individually packaged in sealed pouches. 12 pouches were provided to each subject. Subjects were instructed to apply the solution with the pre-wetted gauze (one pouch) to both nipples approximately 1 hour before sexual activity. The duration of the study was for a period of two weeks. The number of Satisfying Sexual Events (SSE) determined by a Sexual Activity Record (SAR) was recorded. In addition, a modified Female Sexual Function Index (FSFI) desire domain questionnaire was administered. Table 4 summarizes the change in SSEs from baseline. All subjects reported increased nipple sensitivity within 30 minutes after the application of the topical octopamine solution. The nipples remained sensitive up to 3 to 4 hours. Seven subjects reported change in the number of SSEs from baseline. Subjects reporting increase in the number of SSEs also reported increased desire possibly attributed to the hypothesized mechanism of action of oxytocin release as a result of nipple erection.

TABLE 4

| Subject Nr. | Number of SSE (baseline) | Number of SSE (1 week) |
|---|---|---|
| 001 | 1 | 2 |
| 002 | 0 | 1 |
| 003 | 0 | 1 |
| 004 | 2 | 3 |
| 005 | 1 | 1 |
| 006 | 2 | 3 |
| 007 | 1 | 3 |
| 008 | 3 | 4 |
| 009 | 2 | 2 |

Inclusion Criteria for Cancer Related Sexual Adverse Events

CTCAE v4.0: Common Terminology Criteria for Adverse Events version 4.0. is a descriptive terminology developed by the National Cancer Institute. It is considered the standard classification for oncological adverse events as well as outcomes of oncological related clinical studies. As shown in Table 5, two specific questions are related to sexual adverse events in oncology.

TABLE 5

| Adverse Event | 1 | 2 | 3 |
|---|---|---|---|
| Vaginal Dryness* | Mild vaginal dryness not interfering with sexual function | Moderate vaginal dryness interfering with sexual function or causing frequent discomfort | Severe vaginal dryness resulting in dyspareunia or severe discomfort |
| Delayed Orgasm** | Delay in achieving orgasm not adversely affecting relationship | Delay in achieving orgasm adversely affecting relationship | |

*A disorder characterized by an uncomfortable feeling of itching and burning in the vagina
**A disorder characterized by sexual dysfunction characterized by a delay in climax

Example 5

A clinical trial was conducted to assess the efficacy of topical 15% tyramine solution to improve the quality of the female sexual experience when applied to the nipple-areole complex 30-60 minutes before sex. 40 female subjects were recruited to the study, 35 completed. At the start of the trial each subject completed a questionnaire, which included a subset of the Female Sexual Function Index (FSFI). The arousal (questions 3-5), lubrication (questions 7-10), and orgasm (questions 11-13) domains were included. After completing the questionnaire each subject was given 8 pre-wetted gauze pads, individually sealed in a foil pouch, containing either a 15% tyramine hydrochloride solution or a placebo. The subjects were instructed to open one pouch and rub the pad on both nipple-areole complex 30-60 minutes before sex. After four weeks of at-home use each subject returned to the clinic and repeated the questionnaire. Changes in the individual domains of the FSFI after four weeks of using either the 15% tyramine of placebo pads are summarized in Table 6.

TABLE 6

FSFI Domain Changes with 15% Tyramine HCl

| | FSFI | | AROUSAL | | | LUBRICATION | | | ORGASM | | |
|---|---|---|---|---|---|---|---|---|---|---|---|
| Patient | Age | Active/Place | PRE | POST | DELTA | PRE | POST | DELTA | PRE | POST | DELTA |
| 1 | 72 | Placebo | 4.4 | 3.6 | −0.8 | 5.1 | 5.4 | 0.3 | 5.2 | 5.6 | 0.4 |
| 2 | 42 | Placebo | 4 | 4 | 0 | 6 | 6 | 0 | 5.2 | 4.8 | −0.4 |
| 3 | 41 | Placebo | 5.4 | 5.4 | 0 | 6 | 5.7 | −0.3 | 6 | 5.6 | −0.4 |
| 4 | 46 | Placebo | 2.8 | 3.6 | 0.8 | 3 | 4.2 | 1.2 | 4 | 5.2 | 1.2 |
| 5 | 32 | Placebo | 6 | 6 | 0 | 4.8 | 4.8 | 0 | 6 | 6 | 0 |
| 6 | 31 | Placebo | 4 | 4.4 | 0.4 | 4.8 | 5.1 | 0.3 | 4.8 | 5.2 | 0.4 |
| 7 | 42 | Placebo | 5.2 | 5.6 | 0.4 | 6 | 6 | 0 | 6 | 6 | 0 |
| 8 | 37 | Placebo | 3.6 | 4.2 | 0.6 | 6 | 6 | 0 | 4.8 | 4.8 | 0 |
| 9 | 49 | Placebo | 3.6 | 4 | 0.4 | 4.8 | 5.4 | 0.6 | 4 | 5.2 | 1.2 |
| 10 | 49 | Placebo | 4.4 | 4.4 | 0 | 5.4 | 5.4 | 0 | 4.8 | 4.8 | 0 |
| 11 | 51 | Placebo | 1.2 | 1.6 | 0.4 | 1.5 | 1.8 | 0.3 | 1.2 | 1.6 | 0.4 |
| 12 | 43 | Placebo | 4.8 | 5.2 | 0.4 | 5.1 | 5.7 | 0.6 | 6 | 6 | 0 |
| 13 | 37 | Placebo | 5.2 | 4.8 | −0.4 | 6 | 6 | 0 | 6 | 6 | 0 |
| 14 | 47 | Placebo | 4.4 | 5.2 | 0.8 | 5.7 | 6 | 0.3 | 5.2 | 6 | 0.8 |
| 15 | 46 | Placebo | 3.6 | 3.6 | 0 | 4.2 | 3.6 | −0.6 | 4 | 3.6 | −0.4 |
| 16 | 26 | Placebo | 4.4 | 4.4 | 0 | 5.4 | 5.4 | 0 | 6 | 6 | 0 |
| | | AVERAGE-> | 4.19 | 4.38 | 0.19 | 4.99 | 5.16 | 0.17 | 4.95 | 5.15 | 0.20 |
| 17 | 54 | Active | 4 | 4.8 | 0.8 | | | | 4.8 | 5.2 | 0.4 |
| 18 | 67 | Active | 4 | 5.2 | 1.2 | | | | 5.2 | 6 | 0.8 |
| 19 | 41 | Active | 4.8 | 5.6 | 0.8 | | | | 5.2 | 6 | 0.8 |
| 20 | 48 | Active | 3.2 | 4.4 | 1.2 | | | | 4.4 | 4.4 | 0 |
| 21 | 45 | Active | 4.8 | 4 | −0.8 | | | | 4.8 | 5.2 | 0.4 |
| 22 | 38 | Active | 4 | 4.4 | 0.4 | | | | 4 | 5.6 | 1.6 |
| 23 | 41 | Active | 3.6 | 4 | 0.4 | | | | 4 | 4 | 0 |
| 24 | 38 | Active | 2.8 | 2.8 | 0 | | | | 3.2 | 4 | 0.8 |
| 25 | 31 | Active | 6 | 5.2 | −0.8 | | | | 6 | 6 | 0 |
| 26 | 39 | Active | 3 | 3.6 | 0.6 | 4.5 | 4.8 | 0.3 | 4 | 4.4 | 0.4 |
| 27 | 33 | Active | 5.6 | 6 | 0.4 | 4.2 | 5.7 | 1.5 | 6 | 6 | 0 |
| 28 | 40 | Active | 3.6 | 3.6 | 0 | 5.1 | 5.7 | 0.6 | 4.4 | 4.8 | 0.4 |
| 29 | 80 | Active | 3.2 | 3.2 | 0 | 3 | 3.9 | 0.9 | 3.2 | 5.2 | 2 |
| 30 | 22 | Active | 4.8 | 4.8 | 0 | 3 | 4.2 | 1.2 | 4.8 | 6 | 1.2 |
| 31 | 64 | Active | 1.2 | 2.8 | 1.6 | 1.2 | 2.4 | 1.2 | 2.4 | 4 | 1.6 |

TABLE 6-continued

| FSFI Domain Changes with 15% Tyramine HCl | | | | | | | | | | | |
|---|---|---|---|---|---|---|---|---|---|---|---|
| | | FSFI | AROUSAL | | | LUBRICATION | | | ORGASM | | |
| Patient | Age | Active/Place | PRE | POST | DELTA | PRE | POST | DELTA | PRE | POST | DELTA |
| 32 | 63 | Active | 1.8 | 3 | 1.2 | 1.2 | 1.8 | 0.6 | 1.2 | 2.4 | 1.2 |
| 33 | 31 | Active | 3.6 | 4 | 0.4 | 3.9 | 3.9 | 0 | 4 | 4.8 | 0.8 |
| 34 | 37 | Active | 5.2 | 5.6 | 0.4 | 6 | 6 | 0 | 6 | 6 | 0 |
| 35 | 39 | Active | 4 | 4.4 | 0.4 | 6 | 6 | 0 | 5.2 | 5.2 | 0 |
| | | AVERAGE-> | 3.85 | 4.28 | 0.43 | 3.81 | 4.44 | 0.63 | 4.36 | 5.01 | 0.65 |

The invention claimed is:

1. A method for enhancing sexual satisfaction in a female subject, comprising applying an effective amount of a trace amine associated receptor agonist topically to at least a portion of a nipple of the female subject to increase sensitivity of and/or contract a smooth muscle of a nipple areola complex (NAC), wherein the trace amine associated receptor agonist is selected among tyramine, p-tyramine, m-tyramine, N-methyltyramine, 3-methoxy-tyramine, 2-OH-PEA, 3-methoxytyramine or any combination thereof.

2. The method of claim 1, wherein the trace amine associated receptor agonist is present in a composition in a concentration from about 10% to 20% by weight.

3. The method of claim 1, wherein the trace amine associated receptor agonist is applied to the at least the portion of the nipple prior to a sexual activity.

4. The method of claim 1, further comprising erection of the nipple and/or increasing nipple sensitivity via norepinephrine release mediated by the trace amine associated receptor agonist.

5. The method of claim 1, further comprising:
applying an alpha 1 andrenergic receptor agonist, wherein the alpha 1 andrenergic receptor agonist is a synephrine.

6. The method of claim 1, wherein the trace amine associated receptor agonist is formulated as a solution, foam, cream or gel.

* * * * *